(12) United States Patent
Shiraishi et al.

(10) Patent No.: US 10,149,609 B2
(45) Date of Patent: Dec. 11, 2018

(54) SIGNAL PROCESSING DEVICE AND ENDOSCOPE SYSTEM

(71) Applicant: Olympus Corporation, Tokyo (JP)

(72) Inventors: Hiroshi Shiraishi, Hino (JP); Takashi Saito, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 107 days.

(21) Appl. No.: 15/441,950

(22) Filed: Feb. 24, 2017

(65) Prior Publication Data

US 2017/0164817 A1   Jun. 15, 2017

Related U.S. Application Data

(63) Continuation of application No. PCT/JP2016/050507, filed on Jan. 8, 2016.

(30) Foreign Application Priority Data

Jan. 28, 2015 (JP) .................................. 2015-014004

(51) Int. Cl.
*A61B 1/04* (2006.01)
*G02B 23/24* (2006.01)
(Continued)

(52) U.S. Cl.
CPC ............ *A61B 1/04* (2013.01); *A61B 1/00009* (2013.01); *A61B 1/00045* (2013.01); *A61B 1/06* (2013.01);
(Continued)

(58) Field of Classification Search
CPC . H04N 2005/2255; H04N 5/2256; H04N 7/18
See application file for complete search history.

(56) References Cited

U.S. PATENT DOCUMENTS 5,627,583 A * 5/1997 Nakamura ......... A61B 1/00059
348/65

FOREIGN PATENT DOCUMENTS

JP          5-277065 A    10/1993
JP       2007-34520 A     2/2007
(Continued)

OTHER PUBLICATIONS

International Search Report issued in PCT/JP2016/050507 dated Mar. 15, 2016 (in English only).

*Primary Examiner* — Anand S Rao
*Assistant Examiner* — Tyler B Edwards
(74) *Attorney, Agent, or Firm* — Scully, Scott, Murphy & Presser, P.C.

(57) ABSTRACT

A signal processing device processes a signal sent from an imaging device detachably attached to the signal processing device and includes: a signal processing unit configured to rewrite processing contents in accordance with a configuration; configuration memories having different capabilities and configured to store pieces of configuration data corresponding to contents of image processes that are performed in accordance with imaging sensors held by the imaging devices; a configuration controller configured to perform control to subject the signal processing unit to reconfiguration using the configuration data that depends on the imaging sensor of the imaging device attached to the signal processing device among the configuration data; a priority setting unit configured to set priority for each configuration data based on a predetermined condition; and a rewrite controller configured to rewrite the configuration data in the configuration memories based on the priority set by the priority setting unit.

9 Claims, 9 Drawing Sheets (51) Int. Cl.
*H04N 5/225* (2006.01)
*A61B 1/06* (2006.01)
*A61B 1/00* (2006.01)
*H04N 7/18* (2006.01)

(52) U.S. Cl.
CPC ......... *G02B 23/24* (2013.01); *G02B 23/2484* (2013.01); *H04N 5/2256* (2013.01); *H04N 7/18* (2013.01); *H04N 2005/2255* (2013.01)

(56) References Cited

FOREIGN PATENT DOCUMENTS

JP        2007034520 A  *  2/2007
JP        2013-132385 A     7/2013

* cited by examiner

| CONFIGURATION DATA | PRIORITY | |
|---|---|---|
| COMPLEMENTARY | 1 | → FIRST CONFIGURATION MEMORY  Yd |
| PRIMARY | 2 | → FIRST CONFIGURATION MEMORY  Ye |
| MONOCHROME | 3 | → SECOND CONFIGURATION MEMORY  Yf |

SIGNAL PROCESSING DEVICE AND ENDOSCOPE SYSTEM

CROSS-REFERENCE TO RELATED APPLICATION

This application is a continuation of PCT international application Ser. No. PCT/JP2016/050507 filed on Jan. 8, 2016 which designates the United States, incorporated herein by reference, and which claims the benefit of priority from Japanese Patent Applications No. 2015-014004, filed on Jan. 28, 2015, incorporated herein by reference.

BACKGROUND

The present disclosure relates to a signal processing device.

In the medical field, an endoscope system is conventionally used for observation of the inside of a subject. In general, an endoscope captures an in-vivo image in such a manner that an elongated flexible insertion portion is inserted into the subject such as a patient, illumination light supplied by a light source device is emitted from a distal end of the insertion portion, and reflected light of the illumination light is received by an imaging unit at the distal end of the insertion portion. The in-vivo image captured in this way by the imaging unit of the endoscope is displayed on a display of the endoscope system after undergoing a predetermined image process in a processing device of the endoscope system. A user such as a medical doctor observes an organ of the subject based on the in-vivo image displayed on the display.

In the endoscopic examination, various endoscopes are appropriately used in accordance with the purpose of the observation or the observed region. In the endoscope system, the contents of the image processes vary in accordance with imaging sensors of the endoscopes. In order to deal with this feature, a plurality of image processing circuits has been provided in the processing device, or the processing devices themselves have been adapted to the respective types of endoscopes to serve as the individual processing devices. This has led to a demand for a single processing device which has a simpler configuration and can be adapted to a plurality of types of endoscopes.

In order to fulfill this demand, such an endoscope system has been proposed that an image processing circuit of a processing device is configured using a field programmable gate array (FPGA), a memory in which corresponding configuration data are stored is provided in each endoscope, and the processing device causes the FPGA to read the configuration data in the endoscope when the endoscope is connected, and to perform a rewrite to achieve a logic circuit that can execute an image process including the contents corresponding to an imaging sensor of the connected endoscope (for example, refer to JP 2013-132385 A).

There is a need for a signal processing device and an endoscope system in which a single signal processing device can be adapted to a plurality of types of endoscopes, and smooth display of an image is realized without a complicated configuration of the endoscope.

SUMMARY

A signal processing device according to one aspect of the present disclosure processes a signal sent from an imaging device detachably attached to the signal processing device, and includes: a signal processing unit configured to rewrite processing contents in accordance with a configuration; a plurality of configuration memories having different capabilities, each configuration memory being configured to store a plurality of pieces of configuration data corresponding to contents of image processes that are performed in accordance with imaging sensors held by a plurality of the imaging devices attachable to the signal processing device; a configuration controller configured to perform control to subject the signal processing unit to reconfiguration using the piece of configuration data that depends on the imaging sensor of the imaging device attached to the signal processing device among the plurality of pieces of configuration data stored in the configuration memory; a priority setting unit configured to set priority for each of the plurality of pieces of configuration data based on a predetermined condition; and a rewrite controller configured to rewrite the configuration data in the plurality of configuration memories based on the priority set by the priority setting unit.

An endoscope system according to another aspect of the present disclosure includes: a light source device configured to emit illumination light for illuminating an object; an endoscope device including an imaging sensor including a plurality of pixels arranged in a matrix, the imaging sensor being configured to perform a photoelectric conversion on light from the object irradiated with the illumination light to generate an image signal; and a signal processing device configured to process a signal sent from the endoscope device detachably attached to the signal processing device, the signal processing device including: a signal processing unit configured to rewrite processing contents in accordance with a configuration; a plurality of configuration memories having different capabilities, each configuration memory being configured to store a plurality of pieces of configuration data corresponding to contents of image processes that are performed in accordance with imaging sensors held by a plurality of the imaging devices attachable to the signal processing device; a configuration controller configured to perform control to subject the signal processing unit to reconfiguration using the piece of configuration data that depends on the imaging sensor of the endoscope device attached to the signal processing device among the plurality of pieces of configuration data stored in the configuration memory; a priority setting unit configured to set priority for each of the plurality of pieces of configuration data based on a predetermined condition; and a rewrite controller configured to rewrite the configuration data in the plurality of configuration memories based on the priority set by the priority setting unit.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, an endoscope system will be described as an embodiment for practicing the present disclosure (hereinafter referred to as the "embodiment"). The present disclosure is not limited by the embodiments. In the drawings, identical elements are provided with the same reference signs.

First Embodiment

Figure 1:
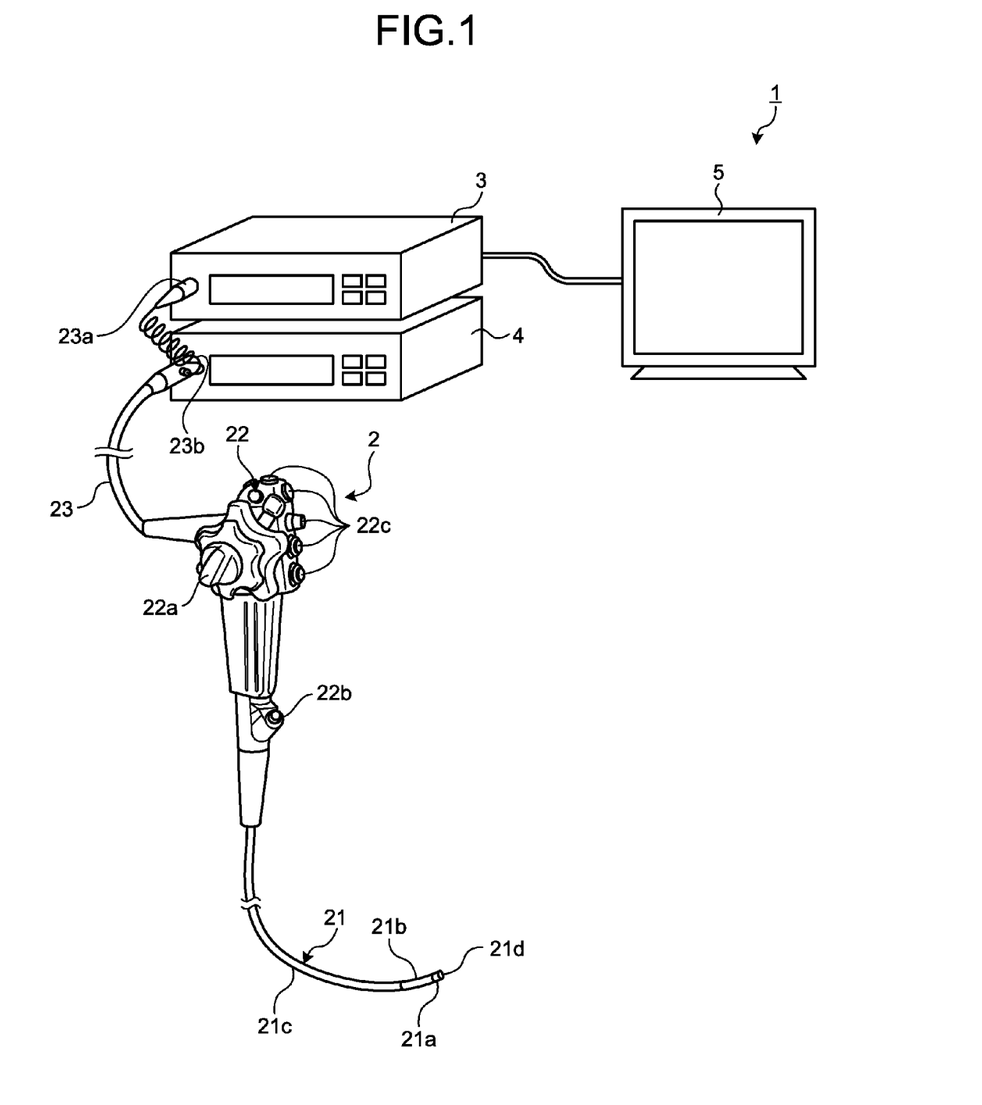
FIG. 1 is a schematic diagram illustrating an overview configuration of an endoscope system according to a first embodiment of the present disclosure.

FIG. 1 is a schematic diagram illustrating an overview configuration of an endoscope system according to a first embodiment of the present disclosure. As illustrated in FIG. 1, an endoscope system 1 according to the first embodiment includes an endoscope 2 (scope), a processing device 3 (signal processing device), a light source device 4, and a display device 5. The endoscope 2 is introduced into a subject and captures the inside of the subject to generate an image signal of the inside of the subject. The endoscope 2 is detachably attached to the processing device 3. The processing device 3 performs a predetermined image process on the image signal sent from the endoscope 2, and controls respective parts of the endoscope system 1. The light source device 4 generates illumination light (observation light) for the endoscope 2. The display device 5 displays an image corresponding to the image signal subjected to the image process by the processing device 3.

The endoscope 2 includes an insertion portion 21 that is inserted into the subject, an operating unit 22 that is a proximal end side of the insertion portion 21 and gripped by a manipulator, and a flexible universal cord 23 extending from the operating unit 22.

The insertion portion 21 is realized by use of an illumination fiber (light guide cable) and an electric cable or the like. The insertion portion 21 has a distal end portion 21*a*, a curve portion 21*b*, and a flexible pipe portion 21*c*. The distal end portion 21*a* has an imaging unit incorporating, for example, a CMOS imaging sensor as an imaging sensor that captures the inside of the subject. The curve portion 21*b* includes a plurality of curve pieces so as to be freely curved. The flexible pipe portion 21*c* is provided on a proximal end side of the curve portion 21*b* and has flexibility. The distal end portion 21*a* is provided with an illumination unit that illuminates the inside of the subject via an illumination lens, an imaging unit that captures the inside of the subject, an opening portion 21*d* communicating with a treatment tool channel, and an air/water supply nozzle (not illustrated).

The operating unit 22 has a curve knob 22*a*, a treatment tool insertion portion 22*b*, and a plurality of switch units 22*c*. The curve knob 22*a* curves the curve portion 21*b* in an up-down direction and a left-right direction. A treatment tool such as living body forceps and a laser scalpel is inserted into a body cavity of the subject through the treatment tool insertion portion 22*b*. A peripheral device such as the processing device 3, the light source device 4, an air supply device, a water supply device, and a gas supply device is operated through the plurality of switch units 22*c*. The treatment tool inserted through the treatment tool insertion portion 22*b* passes through the treatment tool channel provided inside and comes out of the opening portion 21*d* at the distal end of the insertion portion 21.

The universal cord 23 is configured by use of an illumination fiber and an electric cable or the like. The universal cord 23 branches, at a proximal end, into connectors 23*a* and 23*b* that are detachably attached to the processing device 3 and the light source device 4. The universal cord 23 transmits, to the processing device 3 via the connector 23*a*, the image signal captured by the imaging unit provided at the distal end portion 21*a*. The universal cord 23 propagates the illumination light emitted from the light source device 4 to the distal end portion 21*a* via the connector 23*b*, the operating unit 22, and the flexible pipe portion 21*c*.

The processing device 3 performs the predetermined image process on an image signal of the inside of the subject captured by the imaging unit at the distal end portion 21*a* of the endoscope 2 and input via the universal cord 23. The processing device 3 controls the respective parts of the endoscope system 1 based on various instruction signals sent from the switch units 22*c* of the operating unit 22 of the endoscope 2 via the universal cord 23.

The light source device 4 is configured by use of a light source that emits white light and a condenser lens or the like. The light source device 4 supplies the white light from the white light source to the endoscope 2 coupled via the connector 23*b* and the illumination fiber of the universal cord 23 as the illumination light with which the inside of the subject, i.e. an object, is illuminated.

The display device 5 is configured by use of a display or the like using liquid crystal or organic electro luminescence (EL). The display device 5 displays, via a video cable, various kinds of information including the image corresponding to the display image signal subjected to the predetermined image process by the processing device 3. Consequently, the manipulator can observe a desired position in the subject and determine the condition of the desired position by operating the endoscope 2 while watching the image (in-vivo image) displayed by the display device 5.

Figure 2:
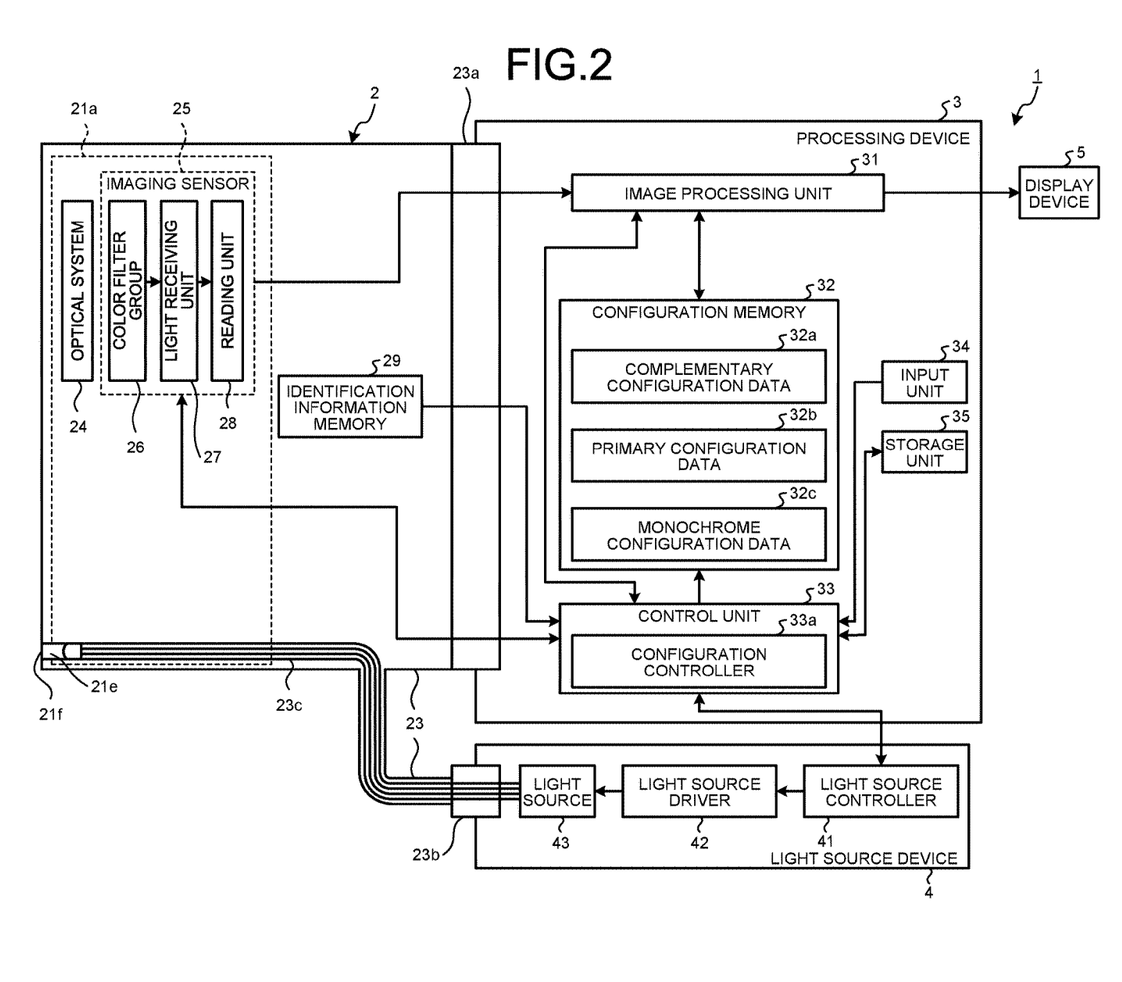
FIG. 2 is a block diagram schematically illustrating a configuration of the endoscope system illustrated in FIG. 1.

Next, the configuration of the endoscope system 1 described in FIG. 1 will be described. FIG. 2 is a block diagram schematically illustrating the configuration of the endoscope system 1 illustrated in FIG. 1.

The endoscope 2 has an optical system 24 and an imaging sensor 25 at the distal end portion 21*a*. A distal end of a light guide cable 23*c* extending from the light source device 4 through the connector 23*b* is located at the distal end portion 21*a*. An illumination lens 21*e* is provided at the distal end of the light guide cable 23*c*. The object is illuminated with the light emitted from the light source device 4 via the light guide cable 23*c* through an illumination window 21*f* at the distal end portion 21*a* of the insertion portion 21. The endoscope 2 also has an identification information memory 29 indicating identification information of the endoscope 2. The identification information memory 29 is a memory that records the identification information of the endoscope 2, and outputs the identification information of the endoscope 2 to the processing device 3 by means of a process of communicating with the processing device 3 when the endoscope 2 is attached to the processing device 3. Alternatively, in some cases, the connector 23a is provided with connection pins in accordance with a rule corresponding to the identification information of the endoscope 2, and the processing device 3 recognizes the identification information of the endoscope 2 based on a connection state between the connection pin close to the processing device 3 and the connection pin close to the endoscope 2 when the endoscope 2 is attached.

The optical system 24 is configured by use of one or more lenses provided at a former stage of the imaging sensor 25, and has an optical zoom function for changing an angle of view and a focus function for changing a focal point.

The imaging sensor 25 has a color filter group 26, a light receiving unit 27, and a reading unit 28. The imaging sensor 25 may be, for example, a CMOS imaging sensor that enables exposure and reading on a horizontal line basis, or may be a CCD imaging sensor.

The color filter group 26 includes a primary color filter group, a complementary color filter group, or a monochrome color filter group. The primary color filter group includes a plurality of primary color filters that transmits light having a primary color component. The complementary color filter group includes a plurality of complementary color filters that transmits light in a wavelength band that is substantially equal to that of the primary color component transmitted by the primary color filters. The monochrome color filter group includes a filter that transmits light in a predetermined wavelength band for the purpose of the enhancement of contrast and shading. Any color filter group 26 is configured in such a manner that the respective filters are arranged in accordance with a pixel array of the light receiving unit 27 to be described later.

In the light receiving unit 27, a plurality of pixels is arranged in a matrix on a light receiving surface. The plurality of pixels receives light that has come from the object irradiated with light and passed through the color filter group 26, and performs a photoelectric conversion on the received light to generate the image signal. The optical system 24 and the color filter group 26 are arranged on the light receiving surface side of the light receiving unit 27.

The reading unit 28 reads the image signal generated by the plurality of pixels of the light receiving unit 27. The image signal read by the reading unit 28 is an electric signal (analog). The imaging sensor 25 also has an AFE unit (not illustrated) that performs a noise removal and an A/D conversion or the like on the electric signal of the image signal read by the reading unit 28, and has a control unit (not illustrated) that controls the operation of the imaging sensor 25 in accordance with a control signal received from the processing device 3. The image signal (digital) generated by the imaging sensor 25 is output to the processing device 3 via a signal cable (not illustrated) and the connector 23a.

The processing device 3 includes an image processing unit 31 (signal processing unit), a configuration memory 32, a control unit 33, an input unit 34, and a storage unit 35.

The image processing unit 31 performs the predetermined image process on a pixel signal (image signal) read by the reading unit 28 of the imaging sensor 25 from the plurality of pixels. The image processing unit 31 performs, on the pixel signal, the image process including an optical black subtraction process, a gain adjustment process, a white balance (WB) adjustment process, a synchronization process for the image signal in a case where the imaging sensor has a Bayer array, a color matrix calculation process, a gamma correction process, a color reproduction process, an edge enhancement process, and a display image signal generation process or the like. The image processing unit 31 is configured by use of an FPGA, i.e. a rewritable programmable logic device capable of rewriting the processing contents in accordance with a configuration. The image processing unit 31 reads configuration data that have been input under the control of a configuration controller 33a to be described later, and performs a rewrite (reconfiguration) of a logic circuit.

Figure 3:
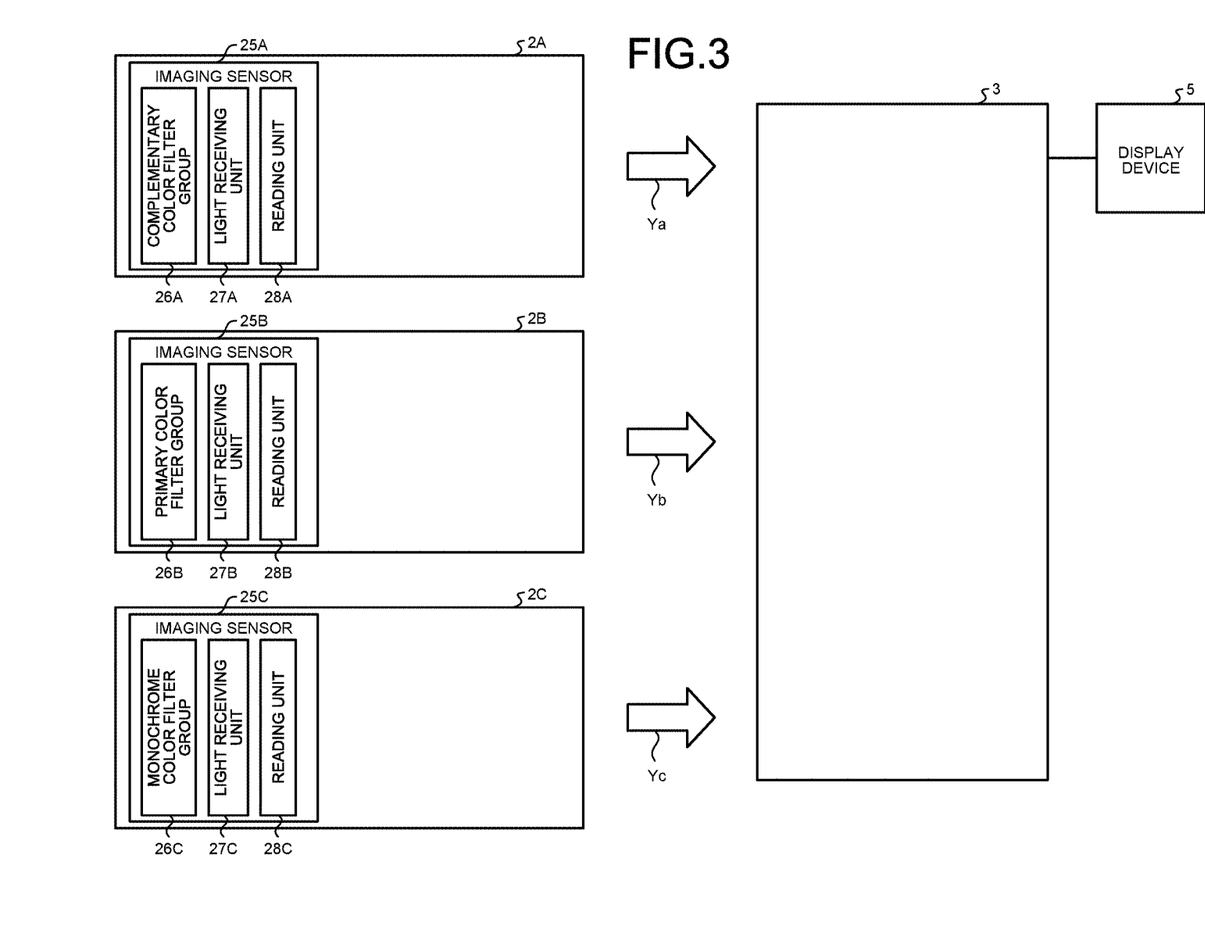
FIG. 3 is a diagram for explaining an endoscope that is attachable to a processing device illustrated in FIG. 2.

The configuration memory 32 stores the configuration data for performing the reconfiguration of the FPGA. The configuration memory 32 stores a plurality of pieces of configuration data corresponding to the contents of the image processes that are performed in accordance with imaging sensors 25 held by a plurality of endoscopes 2 attachable to the processing device 3. As illustrated in FIG. 3, suppose that the endoscope 2 that is attached to the processing device 3 is a first endoscope 2A in which an imaging sensor 25A including a complementary color filter group 26A, a light receiving unit 27A, and a reading unit 28A is mounted, a second endoscope 2B in which an imaging sensor 25B including a primary color filter group 26B, a light receiving unit 27B, and a reading unit 28B is mounted, or a third endoscope 2C in which an imaging sensor 25C including a monochrome color filter group 26C, a light receiving unit 27C, and a reading unit 28C is mounted. In this case, the configuration memory 32 stores complementary configuration data 32a corresponding to the contents of the image process that is performed in accordance with the imaging sensor 25A, primary configuration data 32b corresponding to the contents of the image process that is performed in accordance with the imaging sensor 25B, and monochrome configuration data 32c corresponding to the contents of the image process that is performed in accordance with the imaging sensor 25C. The configuration memory 32 includes a non-volatile memory such as a rewritable flash ROM.

The control unit 33 is realized by use of a CPU or the like. The control unit 33 controls the processing operation of each part of the processing device 3. For example, the control unit 33 transfers instruction information or data to each component of the processing device 3, thereby controlling the operation of the processing device 3. The control unit 33 is coupled to the imaging sensor 25 and the light source device 4 via the respective cables, and also performs control on the imaging sensor 25 and the light source device 4. The control unit 33 has the configuration controller 33a that controls the reconfiguration process in the image processing unit 31.

The input unit 34 is realized by use of an operation device such as a mouse, a keyboard, and a touch panel, and accepts input of various types of instruction information for the endoscope system 1. More specifically, the input unit 34 accepts the input of the various types of instruction information such as subject information (e.g., an ID, a date of birth, and a name or the like), identification information of the endoscope 2 (e.g., an ID and an item to be examined), and examination contents.

The storage unit 35 is realized by use of a volatile memory or a non-volatile memory, and stores various programs for operating the processing device 3 and the light source device 4. The storage unit 35 temporarily stores information during the process performed by the processing device 3. The storage unit 35 records the image signal read by the reading unit 28.

The light source device 4 includes a light source controller 41, a light source driver 42, and a light source 43.

The light source controller 41 controls a process of the light source 43 for emitting the illumination light under the control of the control unit 33. The light source driver 42 supplies predetermined power to the light source 43 under the control of the light source controller 41. The light source 43 is configured, for example, by use of a light source such as a white LED that emits white light and an optical system such as a condenser lens. The light source 43 generates the illumination light that is supplied to the endoscope 2. The object is illuminated, by the light guide cable 23c, with the light emitted from the light source 43 via the connector 23b and the universal cord 23 through the illumination window 21f at the distal end portion 21a of the insertion portion 21. The imaging sensor 25 is arranged in the vicinity of the illumination window 21f.

Next, the control by the configuration controller 33a for the reconfiguration process in the image processing unit 31 will be described. First, when the endoscope 2 is attached to the processing device 3, the configuration controller 33a acquires the identification information of the endoscope 2 indicated by the identification information memory 29 of the attached endoscope 2, and identifies the imaging sensor 25 of the endoscope 2 attached to the processing device 3. As a result, the configuration controller 33a recognizes the contents of the image process that is performed in accordance with the imaging sensor 25 of the endoscope 2, and performs the control to subject the image processing unit 31 to the reconfiguration using the piece of configuration data that depends on the imaging sensor 25 of the endoscope 2 attached to the processing device 3 among the plurality of pieces of configuration data stored in the configuration memory 32. Specifically, the configuration controller 33a causes the image processing unit 31 to read the piece of configuration data that depends on the imaging sensor 25 of the endoscope 2 attached to the processing device 3 among the plurality of pieces of configuration data stored in the configuration memory 32, and to perform the reconfiguration. Consequently, the image processing unit 31 is enabled to execute the image process for the image signal output from the endoscope 2 actually attached to the processing device 3.

In a case where the endoscope 2 is replaced, the configuration controller 33a identifies the imaging sensor 25 of the endoscope 2 connected to the processing device 3 based on the identification information of the endoscope 2 in the identification information memory 29 of the replaced endoscope 2, and causes the image processing unit 31 to read the piece of configuration data that depends on the imaging sensor 25 of the endoscope 2 attached to the processing device 3 among the plurality of pieces of configuration data stored in the configuration memory 32, and to perform the reconfiguration.

In a case where the first endoscope 2A illustrated in FIG. 3 is attached, the configuration controller 33a causes the image processing unit 31 to read the complementary configuration data 32a corresponding to the contents of the image process that is performed in accordance with the imaging sensor 25A, and to perform the reconfiguration. Consequently, the image processing unit 31 is enabled to execute the image process for the image signal output from the first endoscope 2A. In a case where the second endoscope 2B is attached, the configuration controller 33a causes the image processing unit 31 to read the primary configuration data 32b corresponding to the contents of the image process that is performed in accordance with the imaging sensor 25B, and to perform the reconfiguration, whereby the image processing unit 31 is enabled to execute the image process for the image signal output from the second endoscope 2B. In a case where the third endoscope 2C is attached, the configuration controller 33a causes the image processing unit 31 to read the monochrome configuration data 32c corresponding to the contents of the image process that is performed in accordance with the imaging sensor 25C, and to perform the reconfiguration, whereby the image processing unit 31 is enabled to execute the image process for the image signal output from the third endoscope 2C. Therefore, all of the first endoscope 2A, the second endoscope 2B, and the third endoscope 2C, the contents of the image processes of which are different from one another, can be attached to the processing device 3 as indicated by arrows Ya to Yc.

As described above, the endoscope system 1 according to the first embodiment causes the configuration memory 32 of the processing device 3 to store the plurality of pieces of configuration data that depends on the image processes including the contents corresponding to the respective imaging sensors of the plurality of endoscopes to be attached to the processing device 3. Consequently, the endoscope system 1 according to the first embodiment can cause the image processing unit 31 to reconstruct the logic circuit that depends on the image process corresponding to the imaging sensor of the attached endoscope every time any of the endoscopes is attached. Therefore, according to the first embodiment, the single processing device 3 can be adapted to the plurality of types of endoscopes without a complicated configuration of the endoscope. In addition, according to the first embodiment, not the endoscope 2 but the processing device 3 has the configuration data corresponding to the imaging sensor of each endoscope. Therefore, the time for the data transmission/reception between the endoscope and the processing device 3, which has been conventionally required, is no longer needed. Accordingly, the time until the image output can be shortened, and the image can be smoothly displayed.

The example in which the three types of endoscopes can be attached is illustrated in the example of FIGS. 2 and 3. Needless to say, the number of types of endoscopes is not limited to this example. In the first embodiment, the number of types of endoscopes 2 to be attached only needs to be a plural number, and the configuration memory 32 only needs to store in advance the pieces of configuration data corresponding to the respective contents of the image processes corresponding to the imaging sensors of the respective endoscopes.

Second Embodiment

Figure 4:
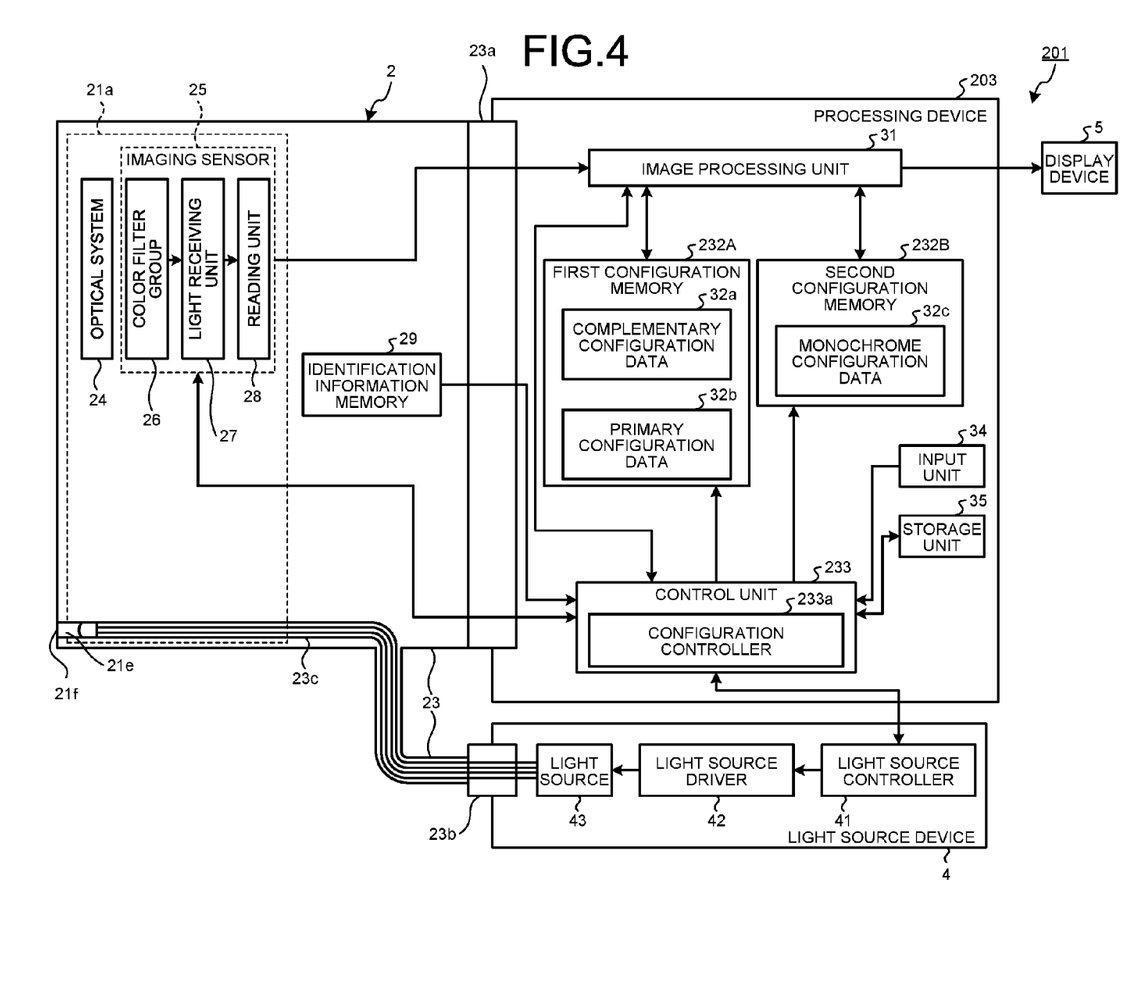
FIG. 4 is a block diagram schematically illustrating a configuration of an endoscope system according to a second embodiment.

Next, a second embodiment will be described. FIG. 4 is a block diagram schematically illustrating a configuration of an endoscope system according to the second embodiment.

As illustrated in FIG. 4, an endoscope system 201 according to the second embodiment has, in place of the processing device 3 illustrated in FIG. 2, a processing device 203 having a plurality of configuration memories that at least partly has a difference in capability. More specifically, the processing device 203 has two configuration memories, i.e. a first configuration memory 232A and a second configuration memory 232B. The processing device 203 also has a control unit 233 having a function similar to that of the control unit 33 illustrated in FIG. 2. The control unit 233 has a configuration controller 233a.

Both the first configuration memory 232A and the second configuration memory 232B include non-volatile memories such as rewritable flash ROMs. The first configuration memory 232A and the second configuration memory 232B have a difference in capability, and the capability of the first configuration memory 232A is higher than that of the second configuration memory 232B. More specifically, the first configuration memory 232A has a fast rate of data transfer to the image processing unit 31 and has a large capacity as compared with the second configuration memory 232B. In the example of FIG. 4, the first configuration memory 232A has such a capacity as to be able to store two pieces of configuration data, and the second configuration memory 232B has such a capacity as to be able to store a single piece of configuration data.

In the endoscope system 201, the higher the capability of the plurality of configuration memories is, the higher the priority of the stored configuration data is. In the example of FIG. 4, with regard to the first configuration memory 232A and the second configuration memory 232B, the first configuration memory 232A having the high capability stores the configuration data of high priority, and the second configuration memory 232B having the low capability stores the configuration data of low priority. The priority of each piece of configuration data is determined in advance based on, for example, a history of the number of times of attachment of the endoscope 2 in which the imaging sensor 25 corresponding to each piece of configuration data is mounted, the number of times of reconfiguration counted for each piece of configuration data, and the number of endoscopes 2 on a type basis owned by a facility in which the endoscope system 201 is installed.

Figure 5:
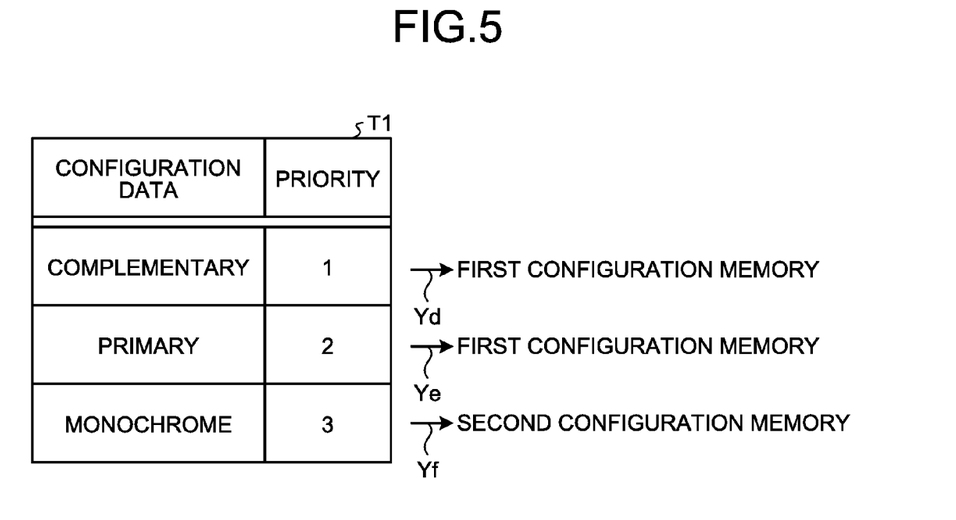
FIG. 5 is a diagram illustrating a table for explaining a storage location of each piece of configuration data.

FIG. 5 is a diagram illustrating a table for explaining a storage location of each piece of configuration data. For example, as in the table T1 of FIG. 5, suppose that the priority is determined in order of the complementary configuration data 32a, the primary configuration data 32b, and the monochrome configuration data 32c. In this case, the complementary configuration data 32a of the first priority and the primary configuration data 32b of the second priority are stored in the first configuration memory 232A as indicated by arrows Yd and Ye, and the monochrome configuration data 32c of the third priority are stored in the second configuration memory 232B as indicated by an arrow Yf.

The configuration controller 233a determines which piece of configuration data is stored in which configuration memory, and causes the image processing unit 31 to read, from either the first configuration memory 232A or the second configuration memory 232B, the piece of configuration data corresponding to the contents of the image process that is performed in accordance with the imaging sensor 25 of the endoscope 2 actually attached to the processing device 203, and to perform the reconfiguration.

As described above, in the second embodiment, the high priority is set for the configuration data corresponding to the imaging sensor 25 of the endoscope 2 having a large number of times of attachment or dominant in number, and the configuration data of high priority are stored in the first configuration memory 232A having a fast rate of data transfer. Consequently, the rate of data transfer to the image processing unit 31 for the configuration data of high priority can be increased, and the time until the image output can be further shortened.

Third Embodiment

Figure 6:
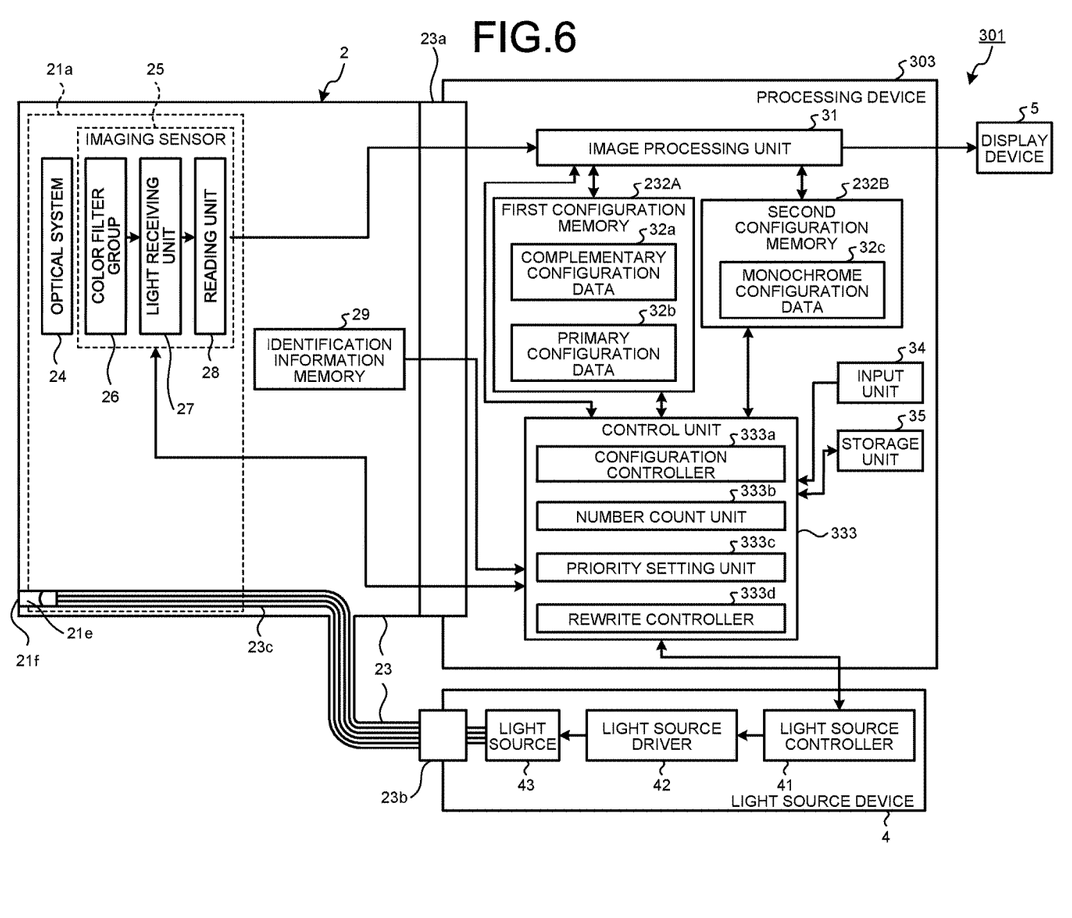
FIG. 6 is a block diagram schematically illustrating a configuration of an endoscope system according to a third embodiment.

Next, a third embodiment will be described. FIG. 6 is a block diagram schematically illustrating a configuration of an endoscope system according to the third embodiment.

As illustrated in FIG. 6, an endoscope system 301 according to the third embodiment includes a processing device 303 having a control unit 333 in place of the processing device illustrated in FIG. 4. The processing device 303 has the control unit 333 including a configuration controller 333a, a number count unit 333b (counting unit), a priority setting unit 333c, and a rewrite controller 333d.

The configuration controller 333a always determines which piece of configuration data is stored in which configuration memory, and causes the image processing unit 31 to read, from either the first configuration memory 232A or the second configuration memory 232B, the piece of configuration data corresponding to the contents of the image process that is performed in accordance with the imaging sensor 25 of the endoscope 2 actually attached to the processing device 303, and to perform the reconfiguration.

The number count unit 333b counts, for each piece of configuration data, the number of times that the configuration controller 333a subjects the FPGA of the image processing unit 31 to the reconfiguration. The number count unit 333b may also count, for each piece of configuration data corresponding to the imaging sensor 25 of the endoscope 2, the number of times that the endoscope 2 is attached to the processing device 303.

The priority setting unit 333c sets the priority for each of the plurality of pieces of configuration data based on a predetermined condition. The priority setting unit 333c sets the priority for each of the plurality of pieces of configuration data in accordance with the count result provided by the number count unit 333b.

The rewrite controller 333d performs control to rewrite the configuration data in the first configuration memory 232A and the second configuration memory 232B. The rewrite controller 333d rewrites the configuration data in the first configuration memory 232A and the second configuration memory 232B based on the priority set by the priority setting unit 333c. With regard to the first configuration memory 232A and the second configuration memory 232B, the rewrite controller 333d rewrites, to the configuration data of high priority, the configuration data in the first configuration memory 232A having the high capability, and rewrites, to the configuration data of low priority, the configuration data in the second configuration memory 232B having the low capability.

Figure 7:
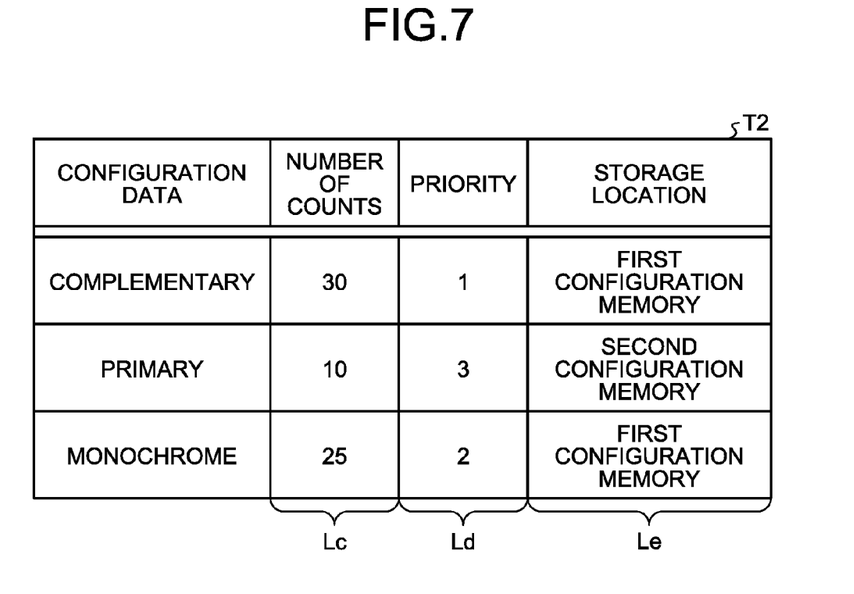
FIG. 7 is a diagram illustrating a table for explaining a setting process that is performed by a control unit illustrated in FIG. 6 for the number of counts, priority, and the storage location with respect to each piece of configuration data.

FIG. 7 is a diagram illustrating a table for explaining a setting process that is performed by the control unit 333 for the number of counts, the priority, and the storage location with respect to each piece of configuration data. The table T2 of FIG. 7 indicates a case where the number count unit 333b counts the number of times that the configuration controller 333a subjects the FPGA of the image processing unit 31 to the reconfiguration, as a result of which a column Lc shows 30 times for the complementary configuration data 32a, 10 times for the primary configuration data 32b, and 25 times for the monochrome configuration data 32c.

In this case, as illustrated in a column Ld, the priority setting unit 333c sets, in descending order of the number of counts counted by the number count unit 333b, the complementary configuration data 32a to the first priority, the monochrome configuration data 32c to the second priority, and the primary configuration data 32b to the third priority. Accordingly, the rewrite controller 333d sets, as indicated in a column Le, the storage locations of the complementary configuration data 32a of the first priority and the monochrome configuration data 32c of the second priority to the first configuration memory 232A, and rewrites the configuration data in the first configuration memory 232A to the complementary configuration data 32a and the monochrome configuration data 32c. The rewrite controller 333d then sets the storage location of the primary configuration data 32b of the third priority to the second configuration memory 232B, and rewrites the configuration data in the second configuration memory 232B to the primary configuration data 32b.

The rewrite process for the configuration data by the rewrite controller 333d may be performed, for example, each time the endoscopic examination is finished. More specifically, the rewrite controller 333d performs the rewrite process for the configuration data when an examination finish button in an operation menu displayed on the display device 5 is selected. Alternatively, the rewrite process for the configuration data by the rewrite controller 333d may be performed at any timing designated by an operator of the endoscope system 301. More specifically, the rewrite controller 333d performs the rewrite process for the configuration data when a predetermined update button in a display menu is selected. Needless to say, the rewrite process for the configuration data by the rewrite controller 333d may be performed in accordance with an instruction from the outside, or may be automatically performed at a preset timing.

As described above, in the third embodiment, the storage location of the configuration data is changed as needed in accordance with the latest number of counts corresponding to each piece of configuration data. Therefore, the rate of data transfer to the image processing unit 31 for the configuration data corresponding to the imaging sensor 25 of the endoscope 2 having a large number of times of attachment or dominant in number is increased more reliably.

Fourth Embodiment

Figure 8:
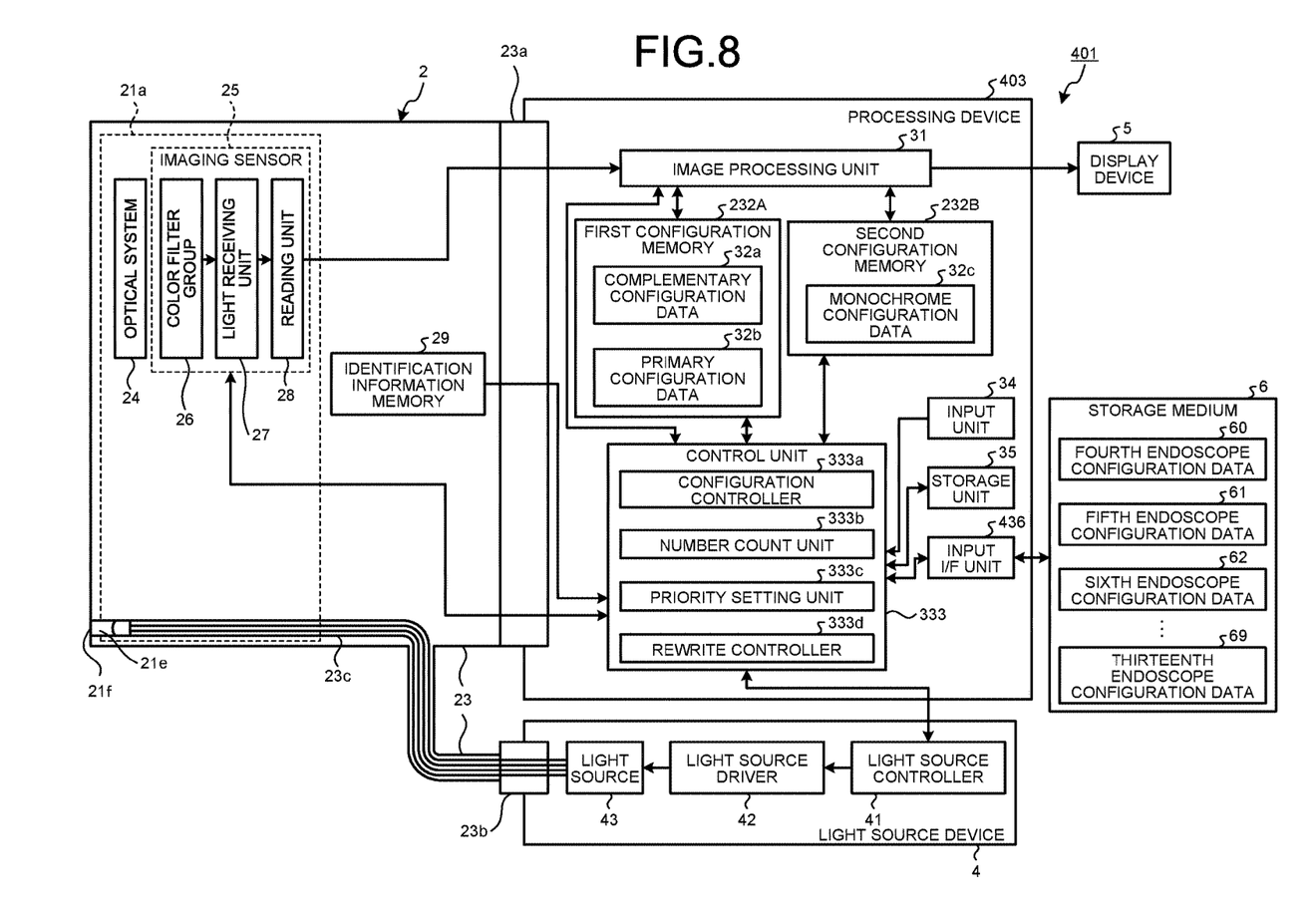
FIG. 8 is a block diagram schematically illustrating a configuration of an endoscope system according to a fourth embodiment.

Next, a fourth embodiment will be described. FIG. 8 is a block diagram schematically illustrating a configuration of an endoscope system according to the fourth embodiment.

As illustrated in FIG. 8, an endoscope system 401 according to the fourth embodiment has a processing device 403 including an input I/F unit 436 that exchanges data with a storage medium 6 such as a memory card. The storage medium 6 can be attached to the processing device 403. The rewrite controller 333d also performs the rewrite control for the data in the attached storage medium 6.

The storage medium 6 stores a plurality of pieces of configuration data which is not held by the processing device 403. The storage medium 6 stores, for example, fourth endoscope configuration data 60 to thirteenth endoscope configuration data 69, i.e. pieces of configuration data that belong to a generation newer than the generation corresponding to each piece of configuration data held by the processing device 403.

The input unit 34 inputs priority information indicating the priority of each of the plurality of pieces of configuration data by means of the operation performed by an operator of the endoscope system 401. More specifically, the operator sets the configuration data to be used and the priority thereof on a predetermined menu, whereby the priority information is input from the input unit 34. The priority setting unit 333c sets the priority for each of the plurality of pieces of configuration data in accordance with the priority information input by the input unit 34.

The rewrite controller 333d rewrites, based on the priority set by the priority setting unit 333c, the configuration data in the first configuration memory 232A and the second configuration memory 232B to the configuration data in the first configuration memory 232A, the configuration data in the second configuration memory 232B, or the configuration data stored in the storage medium 6 connected to the processing device 403.

As described above, according to the fourth embodiment, the processing device 403 can also retrieve the configuration data stored in the external storage medium 6. Therefore, if the configuration data of the endoscope 2 that belongs to a newly released new generation are stored in the storage medium 6 to be attached to the processing device 403, the processing device 403 can be adapted to not only the endoscope 2 that belongs to the prior generation but also the endoscope 2 that belongs to the newly released new generation.

Figure 9:
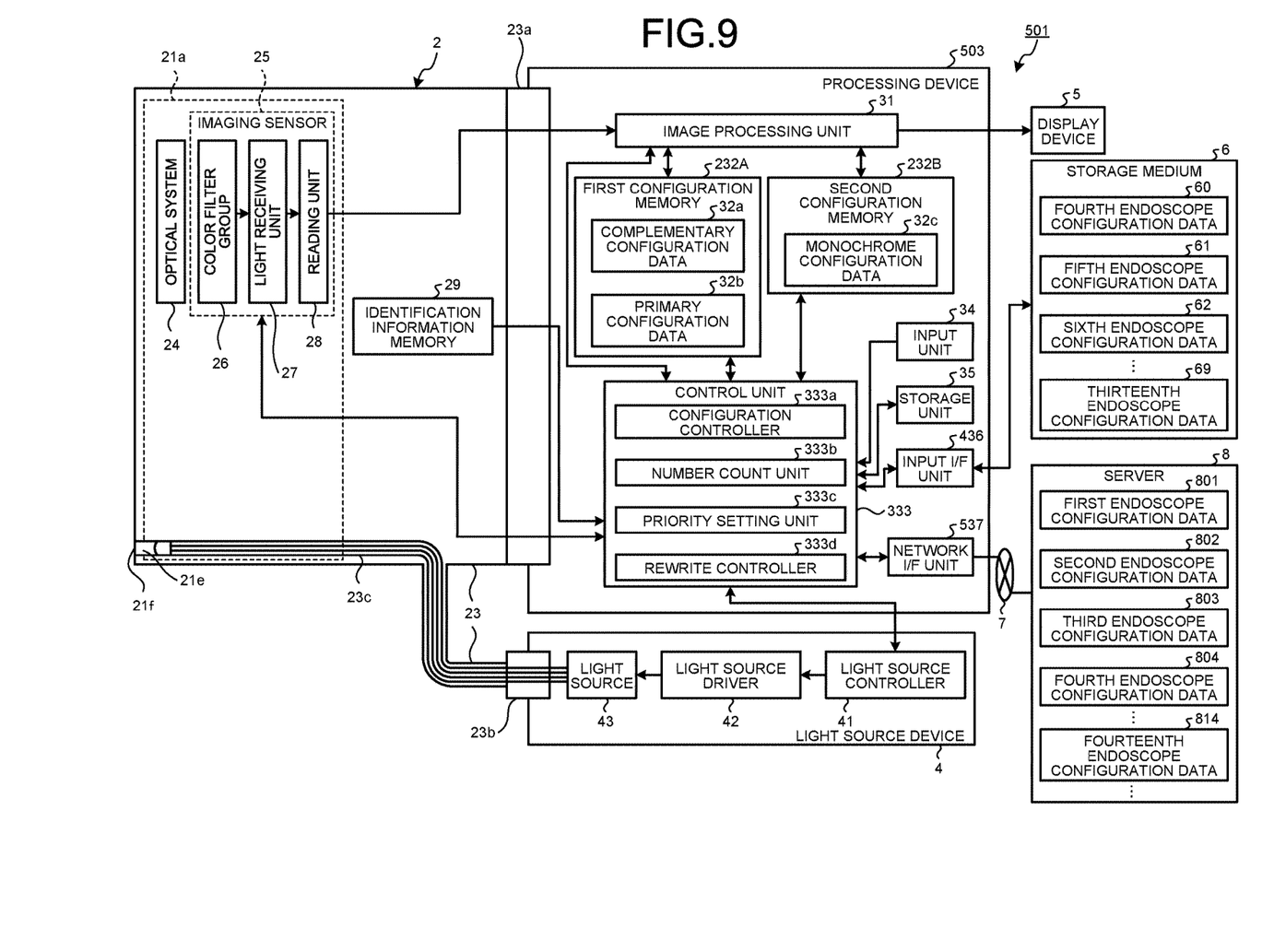
FIG. 9 is a block diagram schematically illustrating another configuration of the endoscope system according to the fourth embodiment.

FIG. 9 is a block diagram schematically illustrating another configuration of the endoscope system according to the fourth embodiment. An endoscope system 501 in FIG. 9 has a processing device 503 further including a network I/F unit 537 and capable of performing a process of communicating with an external server 8 via a network 7. The server 8 holds a plurality of pieces of configuration data, and holds, for example, all the pieces of configuration data corresponding to the imaging sensors 25 of the endoscopes 2 which have been released so far, examples of which include first endoscope configuration data 801 to fourteenth endoscope configuration data 814. The rewrite controller 333d rewrites, based on the priority set by the priority setting unit 333c, the configuration data in the first configuration memory 232A and the second configuration memory 232B to any of the configuration data in the first configuration memory 232A, the configuration data in the second configuration memory 232B, or the configuration data held by the server 8 and acquired via the network 7.

In this case, the processing device 503 can retrieve the configuration data held by the server 8 as well as the configuration data stored in the storage medium 6. Therefore, the processing device 503 can be flexibly adapted to the endoscope 2 that belongs to any generation.

Needless to say, the rewrite controller 333d may acquire, from the server 8, a configuration data group corresponding to the imaging sensors 25 of the respective endoscopes 2 that belong to the newly released new generation from among the pieces of configuration data held by the server 8, and download the acquired configuration data group to the storage medium 6 in advance. In this manner, if the configuration data for the new generation are downloaded to the storage medium 6 in advance, the processing device 503 does not have to connect to the network 7 each time the endoscope 2 that belongs to the new generation is attached to the processing device 503, and acquire, from the server 8, the configuration data corresponding to the imaging sensor 25 of the endoscope 2 that belongs to the new generation, which is efficient.

In the fourth embodiment, the processing devices 403 and 503 may cause the display device 5 to display a menu that enables setting as to which pieces of configuration data are stored in the first configuration memory 232A and the second configuration memory 232B so that the operator himself/herself can select the configuration data to be stored and the storage location. In the same way as the third embodiment, the processing devices 403 and 503 may automatically set which pieces of configuration data are stored in the first configuration memory 232A and the second configuration memory 232B in accordance with the priority set on the basis of the count result of the number count unit 333b.

Execution programs for the respective processes that are executed by the processing devices 3, 203, 303, 403, and 503 according to the embodiments and other components may be recorded and provided in a computer-readable recording medium such as a CD-ROM, a flexible disk, a CD-R, and a digital versatile disk (DVD) in an installable format or executable format file. Alternatively, the execution programs may be stored on a computer connected to a network such as the Internet, downloaded via the network, and provided. Alternatively, the execution programs may be provided or distributed via the network such as the Internet.

In the embodiments, the processing devices 3, 203, 303, 403, and 503 are separate from the light source device 4. However, the processing devices 3, 203, 303, 403, and 503 and the light source device 4 are not limited to this example, and may be integrally configured.

According to the present disclosure, a signal processing device that processes a signal sent from an imaging device detachably attached to the signal processing device has a configuration memory that stores a plurality of pieces of configuration data corresponding to respective contents of image processes that are performed in accordance with imaging sensors of imaging devices to be attached, and performs control to subject a signal processing unit capable of rewriting processing contents in accordance with a configuration to reconfiguration using the piece of configuration data that depends on the imaging sensor of the imaging device attached to the signal processing device among the plurality of pieces of configuration data stored in the configuration memory. Therefore, the single signal processing device can be adapted to a plurality of types of endoscopes, i.e. the imaging devices, and smooth display of an image can be realized without a complicated configuration of the endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A signal processing device that processes a signal sent from an imaging device detachably attached to the signal processing device, the signal processing device comprising:
a signal processing unit configured to rewrite processing contents in accordance with a configuration;
a plurality of configuration memories having different capabilities, each configuration memory being configured to store a plurality of pieces of configuration data corresponding to contents of image processes that are performed in accordance with imaging sensors held by a plurality of the imaging devices attachable to the signal processing device;
a configuration controller configured to perform control to subject the signal processing unit to reconfiguration using the piece of configuration data that depends on the imaging sensor of the imaging device attached to the signal processing device among the plurality of pieces of configuration data stored in the configuration memory;
a priority setting unit configured to set priority for each of the plurality of pieces of configuration data based on a predetermined condition; and
a rewrite controller configured to rewrite the configuration data in the plurality of configuration memories based on the priority set by the priority setting unit.

2. The signal processing device according to claim 1, wherein
the higher the capability of the plurality of configuration memories is, the higher the priority of the stored configuration data is.

3. The signal processing device according to claim 2, wherein
the rewrite controller rewrites, to the configuration data of high priority, the configuration data in the configuration memory having a high capability among the plurality of configuration memories, and rewrites, to the configuration data of low priority, the configuration data in the configuration memory having a low capability among the plurality of configuration memories.

4. The signal processing device according to claim 2, wherein
a storage medium that stores a plurality of pieces of configuration data is attachable to the signal processing device, and
the rewrite controller rewrites, based on the priority set by the priority setting unit, the configuration data in the plurality of configuration memories to either the configuration data in the plurality of configuration memories or the configuration data stored in the storage medium.

5. The signal processing device according to claim 2, wherein,
the signal processing device is connectable to an external device that holds the plurality of pieces of configuration data via a network, and
the rewrite controller rewrites, based on the priority set by the priority setting unit, the configuration data in the plurality of configuration memories to either the configuration data in the plurality of configuration memories or the configuration data held by the external device and acquired by the signal processing device via the network.

6. The signal processing device according to claim 2, further comprising a counting unit configured to count, for each piece of configuration data, the number of times that the signal processing unit is subjected to the reconfiguration, wherein
the priority setting unit sets the priority for each of the plurality of pieces of configuration data based on a count result provided by the counting unit.

7. The signal processing device according to claim 2, further comprising a counting unit configured to count, for each piece of configuration data corresponding to the imaging sensor of the imaging device, the number of times that the imaging device is attached to the signal processing device, wherein
the priority setting unit sets the priority for each of the plurality of pieces of configuration data based on a count result provided by the counting unit.

8. The signal processing device according to claim 2, further comprising an input unit configured to input priority information indicating the priority of each of the plurality of pieces of configuration data, wherein
the priority setting unit sets the priority for each of the plurality of pieces of configuration data in accordance with the priority information input by the input unit.

9. An endoscope system comprising:
a light source device configured to emit illumination light for illuminating an object;
an endoscope device including an imaging sensor including a plurality of pixels arranged in a matrix, the imaging sensor being configured to perform a photo-electric conversion on light from the object irradiated with the illumination light to generate an image signal; and
a signal processing device configured to process a signal sent from the endoscope device detachably attached to the signal processing device, the signal processing device including: a signal processing unit configured to rewrite processing contents in accordance with a configuration; a plurality of configuration memories having different capabilities, each configuration memory being configured to store a plurality of pieces of configuration data corresponding to contents of image processes that are performed in accordance with imaging sensors held by a plurality of the imaging devices attachable to the signal processing device; a configuration controller configured to perform control to subject the signal processing unit to reconfiguration using the piece of configuration data that depends on the imaging sensor of the endoscope device attached to the signal processing device among the plurality of pieces of configuration data stored in the configuration memory; a priority setting unit configured to set priority for each of the plurality of pieces of configuration data based on a predetermined condition; and a rewrite controller configured to rewrite the configuration data in the plurality of configuration memories based on the priority set by the priority setting unit.

* * * * *